United States Patent
Mock et al.

[11] Patent Number: 5,836,878
[45] Date of Patent: Nov. 17, 1998

[54] HEAD RESTRAINT METHOD AND APPARATUS FOR USE IN MRI

[75] Inventors: Bryan J. Mock, Monona; William G. Irwin, Jr., Madison, both of Wis.

[73] Assignee: Wisconsin Alumni Research Foundation, Madison, Wis.

[21] Appl. No.: 909,190

[22] Filed: Aug. 11, 1997

[51] Int. Cl.⁶ .................................................. H61B 5/055
[52] U.S. Cl. ............................ 600/415; 433/24; 600/421
[58] Field of Search ..................................... 600/407, 410, 600/415, 421, 422; 433/24, 33, 29, 34, 44; 378/38, 170, 205; 606/130

[56] References Cited

U.S. PATENT DOCUMENTS

| | | | |
|---|---|---|---|
| 3,614,950 | 10/1971 | Rabey | 606/130 |
| 3,617,742 | 11/1971 | Schulman et al. | 250/61.5 |
| 3,974,388 | 8/1976 | Distler et al. | 250/445 T |
| 4,782,503 | 11/1988 | Molitor et al. | 378/169 |
| 4,841,965 | 6/1989 | Jacobs | 128/303 B |
| 4,869,247 | 9/1989 | Howard et al. | 128/303.1 |
| 4,971,060 | 11/1990 | Schneider et al. | 128/653.1 |
| 5,050,605 | 9/1991 | Eydelman et al. | 128/653 |
| 5,085,219 | 2/1992 | Ortendahl et al. | 128/653.5 |
| 5,090,047 | 2/1992 | Angotti et al. | 378/170 |
| 5,152,288 | 10/1992 | Hoenig et al. | 600/407 |
| 5,176,515 | 1/1993 | Andrews | 433/24 |
| 5,185,577 | 2/1993 | Minemura | 324/318 |
| 5,221,902 | 6/1993 | Jones et al. | 324/318 |
| 5,311,868 | 5/1994 | Carbini et al. | 600/422 |
| 5,357,958 | 10/1994 | Kaufman | 128/653.2 |
| 5,361,765 | 11/1994 | Herlihy et al. | 128/653.5 |
| 5,370,117 | 12/1994 | McLaurin | 128/653.1 |
| 5,370,118 | 12/1994 | Vij et al. | 128/653.5 |
| 5,379,767 | 1/1995 | Derby et al. | 128/653.5 |
| 5,379,768 | 1/1995 | Smalén | 128/653.5 |
| 5,400,787 | 3/1995 | Marandos | 128/653.5 |
| 5,435,302 | 7/1995 | Lenkinski et al. | 128/653.5 |
| 5,437,280 | 8/1995 | Hussman | 128/653.2 |
| 5,464,411 | 11/1995 | Schulte et al. | 606/130 |
| 5,500,884 | 3/1996 | Guenther et al. | 378/38 |
| 5,513,240 | 4/1996 | Hausmann et al. | 378/170 |
| 5,531,229 | 7/1996 | Dean et al. | 606/130 |
| 5,566,681 | 10/1996 | Manwaring et al. | 128/845 |
| 5,588,430 | 12/1996 | Bova et al. | 128/653.1 |
| 5,619,996 | 4/1997 | Beresten | 128/653.5 |
| 5,629,972 | 5/1997 | Hausmann et al. | 378/170 |
| 5,706,811 | 1/1998 | Takeda et al. | 600/407 |
| 5,707,334 | 1/1998 | Young | 600/9 |

*Primary Examiner*—Brian Casler
*Attorney, Agent, or Firm*—Whyte Hirschboeck Dudek, S.C.

[57] ABSTRACT

A method and apparatus is disclosed for immobilizing a patient's head within an MRI headcoil to avoid the use of imaging enhancements that compensate for patient movement. The apparatus includes a bite plate having a dental impression of the particular patient at one end, and at the other end, the bite plate is attached to a mounting bracket assembly. The mounting bracket assembly is rigidly attached to the MRI headcoil. The mounting bracket assembly includes a main bracket, an intermediary bracket, and a clamping plate. The bite plate is adjustably mounted to the intermediary bracket, which in turn is adjustably mounted to the main bracket to provide both approximate adjustments and precise adjustments, respectively. The clamping plate attaches the mounting bracket assembly to at least one rung of the headcoil. A patient adjustable retainer is provided for locking the bite plate to the intermediary bracket and providing a method of allowing the technician or the patient to perform the precise adjustments so that the patient is most comfortable during a lengthy MRI. Although the device is custom fitted for each patient, aside from the actual dental impression, the device is completely reusable.

15 Claims, 4 Drawing Sheets

HEAD RESTRAINT METHOD AND APPARATUS FOR USE IN MRI

BACKGROUND OF THE INVENTION

The present invention relates generally to Magnetic Resonance Imaging (MRI), and more particularly, to a method and apparatus for immobilizing a patient's head within an MRI headcoil during imaging.

The use of functional Magnetic Resonance Imaging (fMRI) to study brain function is a rapidly growing scientific enterprise. Within this scientific field there is much literature documenting the problems associated with head movement. Because of the nature of the imaging modality, head movement can result in image data patterns which appear as functional activity, when in fact they are purely artifactual. Post-processing techniques designed to "remove" the effects of head movement are controversial, computer-intensive, and introduce other artifacts which may be as undesirable as the artifact from head movement, such as elimination of real activation patterns. It is a general and non-controversial conclusion by those in the neuroimaging community that prevention of head movement, rather than attempts to correct it, is the goal. As fMRI begins to be used in more clinical settings, such as presurgical planning, with patients who are likely to have additional difficulty in keeping still (e.g., patients with tremors), head immobilization will be particularly critical.

Various other medical procedures such as radiographic imaging require stabilization or immobilization of particular body parts. Traditional stabilization or positioning techniques for such procedures on body parts other than the head, include providing padded supports or contoured mattresses. However, when the head is involved, these techniques are not very effective because of equipment size limitations and the general difficulty in keeping the patient from moving the head even in a support. Standard MRI headcoils are quite restrictive. That is, in order to provide a satisfactory signal-to-noise ratio, it is desirable to produce the headcoils as small as possible. For example, see U.S. Pat. No. 5,619,996. Therefore, it has been proven difficult to provide a reliable head restraint in such confining headcoils.

This problem is exaggerated in fMR imaging due to the length of time required for fMRI—up to two hours. If the head is allowed to move during MR imaging, the resultant cross-sectional image will be distorted and/or blurred and will require correction. Any movements by the patient during imaging requires corrective action. In a research setting, typically after an MRI is complete, special imaging enhancement software is required to compensate for patient movement during any one MRI scan. There are typically 8–10 scans per exam and each scan can take from 20 seconds to 10 minutes. Although patient movement during a single scan can be corrected, any movement that occurs from one scan to another results in either repeating the entire 2 hour exam, or discarding that scan. In a clinical setting, if there is any movement, the scan is discarded and no attempt at correction is made. The entire scan must be redone. It would be desirable to minimize all movement by the patient in order to avoid discarding tests and artificially correcting images.

A standard head immobilization device used with MR imaging systems is one where a VELCRO® strap is placed around the forehead. However, the degree of head movement that is still possible with such a strap, which occurs frequently, is beyond the limits allowed for the collection of accurate fMRI data.

Another common procedure for immobilizing the head involves the use of a number of invasive fixating pins mounted in the skull. Although acceptable for surgery, this method is unacceptable for standard MRI scans not only because of the invasiveness, but also because metal components are a source of interference in MRI.

Another method for immobilizing the head is disclosed in U.S. Pat. No. 4,869,247. However, such a device is large, bulky, and interferes with the standard MRI headcoil. Further, such a device is not usable with a patient in the supine position.

Other attempts at immobilizing a patient's head include the use of vacuum holders with a mouthpiece for leveling as disclosed in U.S. Pat. No. 4,841,965, the disadvantage of which is the need for a constant vacuum supply and the difficulty in adapting it with standard MRI headcoils. Further, the set-up is time consuming and rather complex. U.S. Pat. No. 5,400,787 shows an inflatable sleeve used for stability. However, such this apparatus would not be acceptable for use on the head because of general discomfort to the patient caused by heat accumulation and lack of air circulation within the sleeve.

It would be desirable to have a method and apparatus to immobilize the human head during MR imaging which is easy to use, does not traumatize the patient, does not require surgery, places the patient in a relatively comfortable position, and is readily adaptable to standard MRI equipment.

SUMMARY OF THE INVENTION

The present invention provides a method and apparatus for immobilizing a patient's head within an MRI headcoil that overcomes the aforementioned problems and does so with a configuration uniquely sized to fit within the existing standard headcoils used in an MRI.

The head restraint disclosed includes a mounting bracket assembly having a number of slots engageable with the rungs of a headcoil and having a clamping plate to firmly secure at least one of the headcoil rungs between the mounting bracket assembly and the clamping plate. A bite plate is provided which has one end capable of engagement within a patient's mouth to restrain the head, and a second end extending outwardly and adjustably mounted to the mounting bracket assembly to allow fore and aft adjustment of the bite plate.

The mounting bracket assembly includes a main bracket, an intermediary bracket, and the clamping plate. The main bracket is placed over the outside of the headcoil and the approximate, or rough adjustments of the mounting bracket assembly to the patient. The bite plate is adjustably mounted onto the intermediary bracket with the use of an adjustable retainer that locks the bite plate to the intermediary bracket while allowing the technician, or the patient, to perform precise fore and aft adjustments of the bite plate to the patient. The bite plate includes a replaceable dental impression of the patient's teeth so that the head restraint of the present invention is readily customized for each individual patient. In this manner, the present invention can be reused to position the patient in a relatively consistent position during later exams.

In general, a head restraint is disclosed for use in an MRI including a main bracket having two outwardly extending chamfered corners. Each of the chamfered corners are capable of engaging a headcoil rung. The main mounting bracket includes another channel which is generally centrally located between the chamfered corners and sized to accept a third headcoil rung therein. A means for locking at least one of the headcoil rungs to the main mounting bracket is provided, as well as a means for engaging the main mounting bracket to the patient's head for a custom fit, which thereby immobilizes the patient's head with reference to the headcoil. at least one of the headcoil rungs to the main mounting bracket is provided, as well as a means for engaging the main mounting bracket to the patient's head for a custom fit, which thereby immobilizes the patient's head with reference to the headcoil.

In accordance with another aspect of the invention, a method of imaging a patient's head using a standard MRI headcoil is disclosed in which there is usually no need to use imaging enhancement software to compensate for patient movement during the MRI. The method includes the steps of preparing a dental impression compound and affixing the dental impression compound onto a bite plate. While the dental impression compound is still pliable, an impression of the patient's teeth are taken while the dental impression compound is affixed to the bite plate. After allowing the dental impression to harden, the bite plate is rigidly attached to the headcoil and is adjusted to comfortably fit the patient. The patient then engages the dental impression by biting the bite plate to rigidly fix the patient's head with reference to the headcoil. The relatively fixed patient head can then be imaged without the need for imaging enhancements that compensate for movement. There is also no need to repeat scans because of movement from one scan to another.

The present invention is particularly useful in the field of fMRI, where a cognitive study of brain activity is conducted using novel stimuli. During such a study, if a patient moves at all from one scan to the next, the entire study must be discarded and cannot be repeated with the same patient because the stimuli are no longer novel. The present invention solves this problem by maintaining head stability.

MRI testing of the present device demonstrated that there were no known signal artifacts introduced by the of device aside from some minor susceptibility dephasing, or signal drop-out, near the patent's lips.

Various other features, objects and advantages of the present invention will be made apparent from the following detailed description and the drawings.

BRIEF DESCRIPTION OF THE DRAWINGS

The drawings illustrate the best mode presently contemplated for carrying out the invention.

In the drawings.

DETAILED DESCRIPTION OF THE PREFERRED EMBODIMENT

Figure 1:
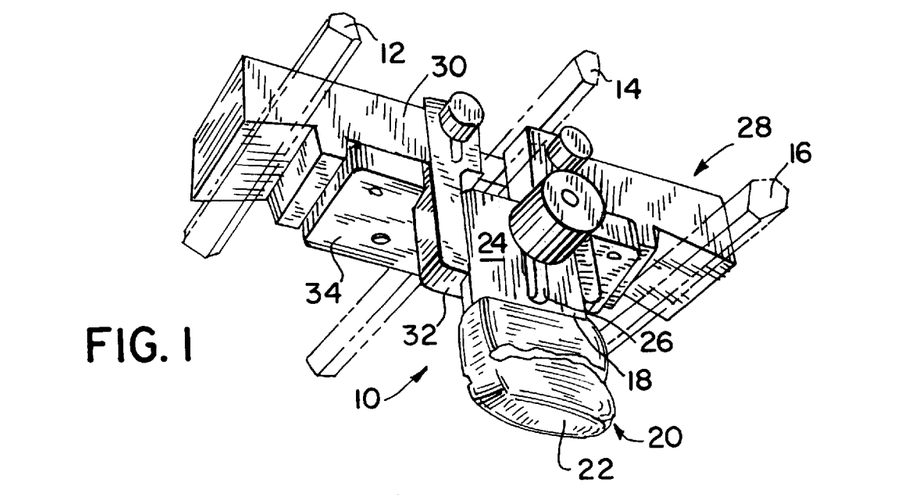
FIG. 1 is a perspective view showing a head restraint according to the present invention mounted on headcoil rungs.

The present invention includes a head restraint for use in Magnetic Resonance Imaging (MRI). Accordingly, all the components of the head restraint are comprised of non-ferrous materials. Referring to FIG. 1, a head restraint 10, according to the present invention, is shown attached to a portion of an MRI headcoil having rungs 12, 14, and 16 shown in phantom. For simplicity, the headcoil rungs are only partially shown, but it is understood the headcoil depicted is similar to that commonly used in the MRI industry. The head restraint 10 has a bite plate 18 having a first end 20 fitted with a replaceable dental impression compound 22 capable of engagement with a patient, and a second end 24 extending outwardly from the patient and having an elongated adjustment slot 26 therein. A mounting bracket assembly 28 includes a main bracket 30, an intermediate bracket 32 and a clamping bracket 34 for locking the head restraint 10 to headcoil rung 14.

Figure 2:
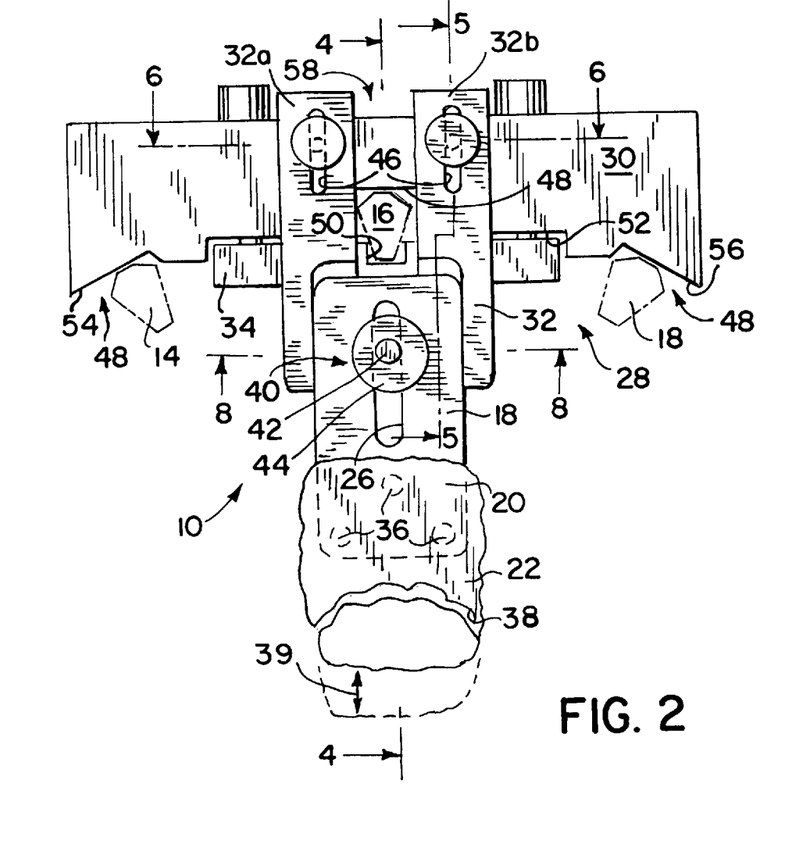
FIG. 2 is a top view of the apparatus of FIG. 1.

FIG. 2 shows a top view of the apparatus 10 for immobilizing a patient's head within an MRI headcoil. The bite plate 18 has a number of openings 36 in the first end 20 which assist in removably attaching the dental impression compound 22 onto the bite plate 18 when the dental impression compound is originally formed and is in its softened state. The dental impression compound used is that which is commonly used in the dental industry. With the bite plate 18 removed from the head restraint 10, and after the dental impression compound 22 is applied to the bite plate 18, an inverse dental impression 38 of a patient's bite is made in the compound while it is still pliable.

A patient adjustable retainer 40 is used to lock the bite plate 18 to the intermediate bracket 32. In a preferred embodiment, the patient adjustable retainer 40 includes a threaded stud 42 and a retaining nut 44. The stud 42 acts as a guide to fit the bite plate 18 onto the intermediary bracket 32. In this manner, a patient or an MRI technician, can easily fit the bite plate 18 onto the head restraint 10 with little effort. The bite plate 18 can be adjusted in either a fore or aft direction 39 about stud 42 along slot 26 to provide an accurate and comfortable fit for the patient.

Whereas the adjustable retainer 40 allows for precise adjustments of the bite plate 18 to the patient, the intermediary bracket 32 is also adjustably mounted, but for making base, approximate adjustments of the mounting bracket assembly 28 to the patient before making the more precise adjustments with the retainer 40. The intermediary bracket 32 has a pair of adjustment slots 46 and is mounted to the main bracket 30 such that it also is adjustable fore and aft in the direction 39. In this manner, the bite plate 18 can be retracted far enough so that the patient can enter the headcoil with the head restraint already attached to the headcoil. This base adjustment is intended to be made by the MRI technician to position the bite plate 18 in close proximity of its ultimate position, while the more precise adjustments made with the retainer 40 are designed to be made by the patient for more accurate placement so that the dental impression 38 is comfortably aligned with the patient's bite.

The main bracket 30 has a number of rung slots 48, each configured to accept a headcoil rung 14, 16, and 18 therein. The clamping bracket, or plate, 34 has a centrally located channel 50 for receiving an inside surface of the center headcoil rung 16 therein such that the headcoil rung 16 is positively engaged on a number of sides to prevent relative movement of the head restraint 10 with respect to the entire headcoil. The main mounting bracket 30 also has an undercut 52 about the central channel 48. The undercut 52 provides firm engagement of the clamping 34 to the main mounting bracket 30 which provides additional stability between the head restraint 10 and the headcoil. The multiple rung slots 48 include two outwardly extending chamfered corners 54 and 56, wherein corner 54 is designed to engage a headcoil rung 14 and corner 56 is designed to engage a headcoil rung 18. The third rung slot 48 is generally centrally located in the main bracket 30. The central rung slot 48 acts in conjunction with the channel 50 of clamping plate 34 and an opening 58 between legs 32a and 32b of the intermediary bracket 32, to accept and lock the third headcoil rung 16 into the head restraint 10. In this manner, the head restraint 10 can be firmly engaged to the headcoil.

Figures 3, 5:
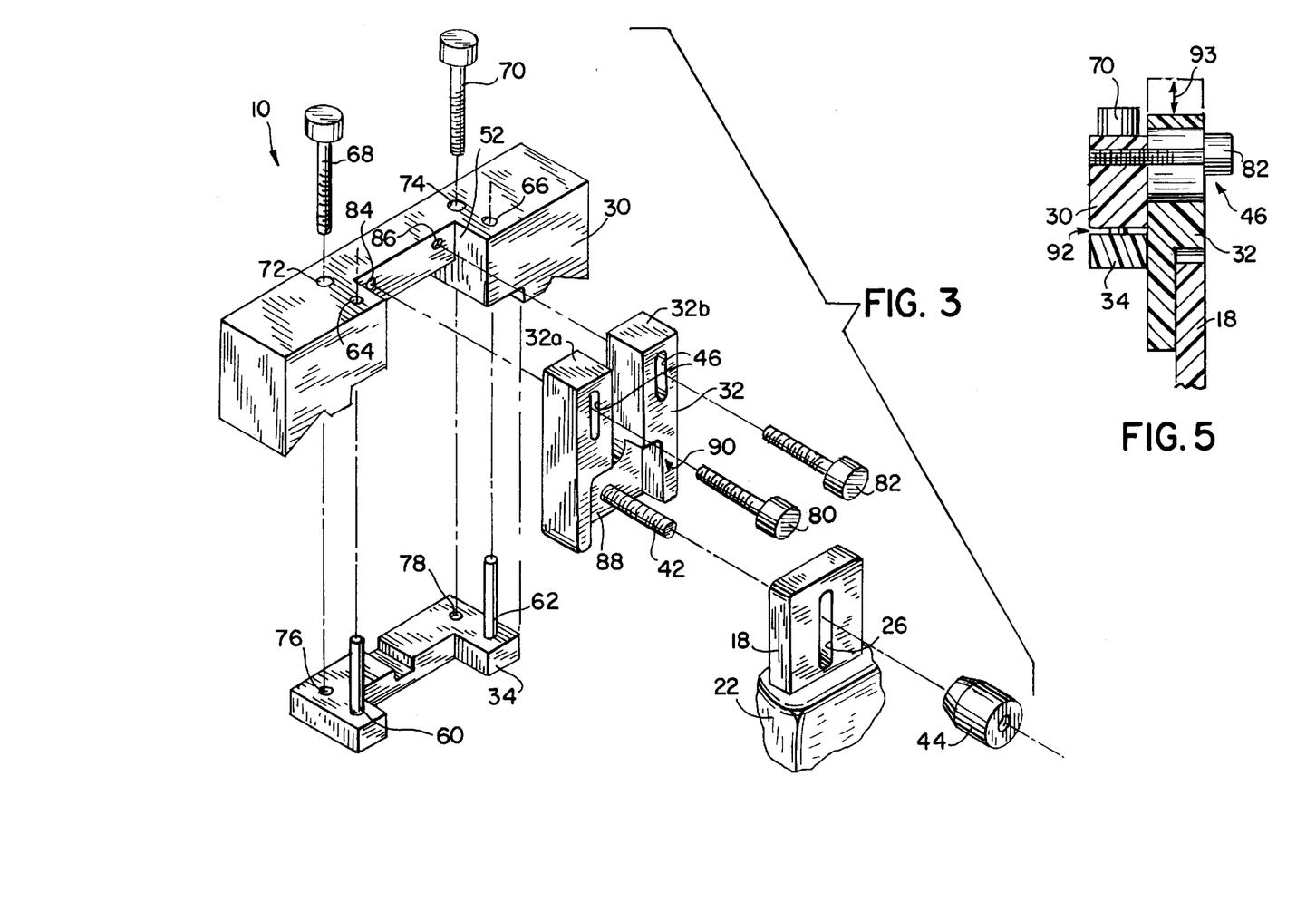
FIG. 3 is an exploded, perspective view of the head restraint of FIG. 1.
FIG. 5 is a cross-sectional view of a portion of FIG. 2 taken along line 5—5.

Referring to FIG. 3, an exploded perspective view shows the main components of the head restraint 10. The clamping plate 34 has a pair of guide pins 60 and 62 for engagement with a corresponding pair of passages 64 and 66 in main bracket 30. The guide pins 60 and 62 not only provide ease of assembly about the headcoil rung, but also provide additional stability to the assembly. A pair of cap screws 68 and 70 are inserted through passages 72 and 74 of the main bracket 30 and engage threaded openings 76 and 78 of the clamping plate 34. Accordingly, the head restraint 10 is adjustably mounted to the headcoil for movement along the headcoil to compensate for varying head and neck lengths. Once adjusted along the headcoil rungs, the cap screws 68 and 70 are tightened so that the head restraint 10 is firmly engaged to the headcoil.

A second pair of cap screws 80 and 82 are positioned through slots 46 of intermediary bracket 32 and into threaded openings 84 and 86 in the undercut recess 52 of main bracket 30. The intermediary bracket 32 has a threaded stud 42 extending therefrom within a recessed channel 88 to receive the bite plate 18 thereon such that the bite plate 18 is flush with a top surface 90 of the intermediary bracket 32. The recessed channel 88 also acts to prevent lateral movement of the bite plate 18 with respect to the intermediary bracket 32. The threaded stud 42 extends through the adjustment slot 26 of bite plate 18 and is engageable with the retaining nut 44 to retain the bite plate 18 on the intermediary bracket 32. As will be further explained with reference to FIG. 9, the threads of stud 42 and retaining nut 44 are left-handed and have pitch and spacing to accommodate patient use.

Figure 4:
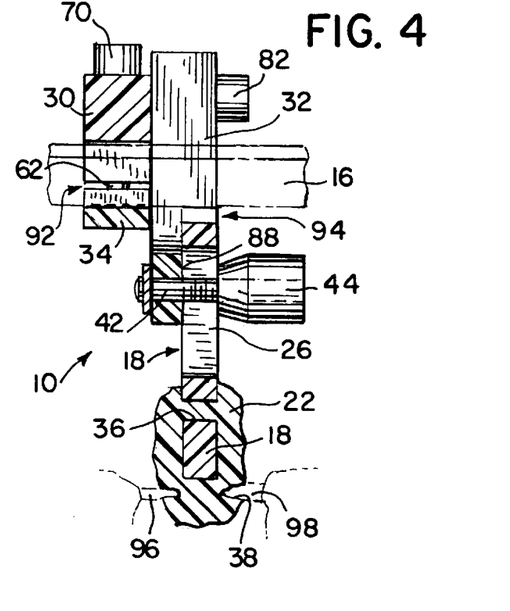
FIG. 4 is a cross-sectional view of FIG. 2 taken along the line 4—4 with teeth shown in phantom engaging a portion of the apparatus.

FIG. 4 shows a cross-sectional view taken down the center of the head restraint 10 of FIG. 2. This view shows the assembled head restraint 10 clamped about MRI headcoil rung 16. Cap screw 70 is shown clamping the rung 16 between the clamping plate 34 and main bracket 30 leaving a slight gap 92 for slight variations in rung width and to ensure the rung is firmly clamped when cap screw 70 is tightened securely. Guide pin 62 is shown in gap 92 between the clamping plate 34 and the main bracket 30. The intermediary bracket 32 is fixed to the main bracket with cap screw 82 and the bite plate 18 is shown within the recessed channel 88 for a flush fit with the intermediary bracket 32 and retained therein by stud 42 and retaining nut 44.

Bite plate 18 is adjustable along adjustment slot 26 for precise placement of the inverse dental impression 38 with the upper teeth 96 and the lower teeth 98 of a patient. Although adjustable by the MRI technician, the size and placement of retaining nut 44 allows the patient to make the finer adjustments so that the patient is most comfortable. A gap 94 is a function of the bite plate 18 position on stud. 42 in slot 26. In a preferred embodiment, the outer circumference of the retaining nut 44 is knurled to accommodate easy finger tightening and loosening. One of the openings 36 in bite plate 18 is shown so that it is evident that when the dental impression compound is pliable, it is retained to the bite plate 18 through these openings 36.

FIG. 5 is a partial sectional view taken along the line 5—5 of FIG. 2 to show the adjustment slot 46 in the intermediary bracket 32. The slot 46 allows the intermediary bracket fore and aft movement 93 so that the MRI technician can make approximate adjustments of the intermediary bracket 32 and bite plate 18 combination with respect to the patient by loosening the cap screw 80, 82.

Figure 6:
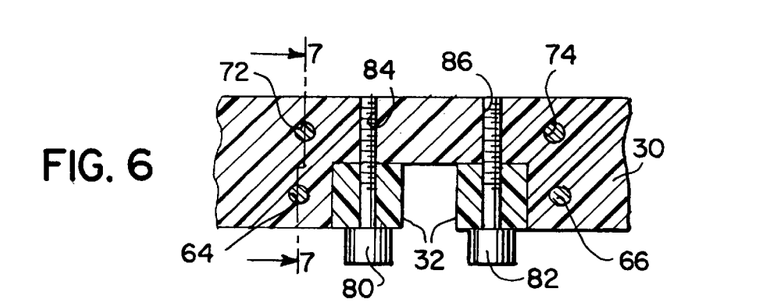
FIG. 6 is a cross-sectional view of a portion of FIG. 2 taken along line 6—6.

FIG. 6 is a partial sectional view taken along line 6—6 of FIG. 2 showing the precise fit between the intermediary bracket 32 and the main bracket 30. The two brackets are shown bolted together with cap screws 80 and 82 in threaded passages 84 and 86. Other passages shown are openings 72 and 74 for the cap screws 68 and 70, FIG. 3, and passages 64 and 66 for the guide pins 60 and 62 of the clamping plate 34.

Figure 7:
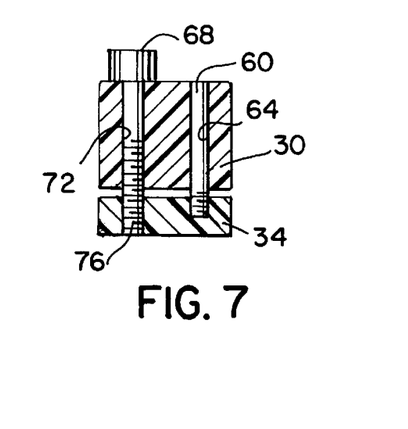
FIG. 7 is a cross-sectional view of FIG. 6 taken along line 7—7.

FIG. 7 is a sectional view taken along line 7—7 of FIG. 6 showing the cap screw 68 in passage 72 and engaging clamping plate 34 in threaded passage 76. The guide pin 60 extending from the clamping plate 34 is shown in passage 64 of the main bracket 30.

Figure 8:
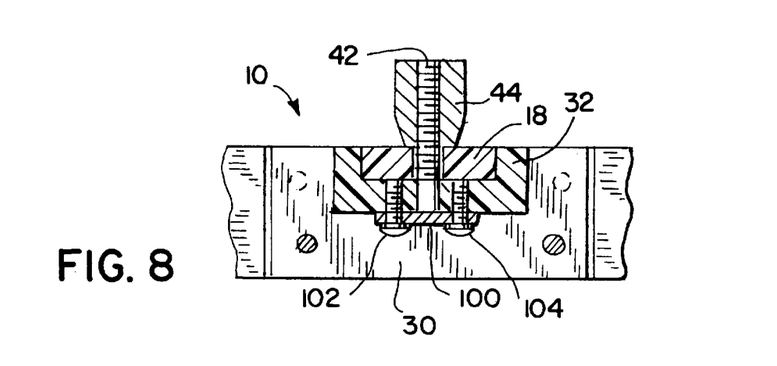
FIG. 8 is a cross-sectional view of a portion of FIG. 2 taken along line 8—8.

FIG. 8 is a partial sectional view of the assembled head restraint 10 taken along line 8—8 of FIG. 2 showing the bite plate 18 mounted on the intermediary bracket 32. The retaining nut 44 is shown threadedly engaged with the threaded stud 42 extending outwardly from the intermediary bracket 32. A stud mounting bracket 100 is retained to the underside of the intermediary bracket 32 by retention screws 102 and 104 for retaining the threaded stud 42 in the intermediary bracket 32.

Figure 9:
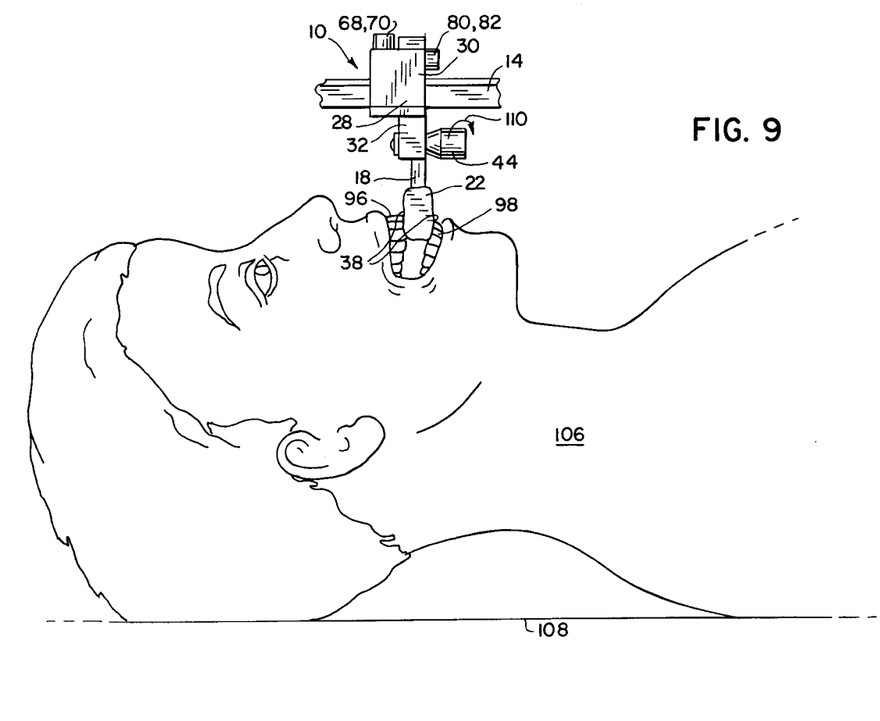
FIG. 9 is a side view of the present invention in use.

FIG. 9 shows the head restraint 10 applied to an MRI headcoil, depicted by a single rung 14 for simplicity, and in use by a patient 106 lying on an MRI bed 108. However, it is understood that FIG. 9 is illustrative of the headcoil only with respect to the point of attachment of the head restraint to the headcoil. In practice, the headcoil encircles the patient's head as shown in U.S. Pat. No. 5,619,996. To apply the head restraint 10, the main bracket 30 is placed on the outside of the rung 14 and the intermediary bracket 32 is placed over the inside surface of rung 14. The clamping plate 34 is also placed over the inside surface of rung 14 and the cap screws 68 and 70 are inserted and tightened to clamp the mounting bracket assembly 28 over rung 14 after the MRI technician makes adjustments of the mounting assembly 28 along the rungs of the headcoil for that patient. The technician then makes approximate adjustments of the bite plate 18 using cap screws 80 and 82 to bring the dental impression 38 in the dental impression compound 22 of the bite plate 18 into close proximity to the patient's teeth 96 and 98. The cap screws 80 and 82 are then tightened and once the patient 106 is orientated in a comfortable position, the technician, or the patient, can then reach upward and loosen the retaining nut 44 to precisely position the dental impression 38 of the bite plate 18 into contact with the patient's teeth 96 and 98. As the patient bites down on the bite plate 18, the patient's head is immobilized within the MRI headcoil. Without the potential of head movement by the patient, the MR imaging can be accomplished without imaging enhancement software to compensate for patient movement.

To accommodate most patients who feel comfortable turning the retaining nut 44 in a clockwise direction as indicated by arrow 110 to loosen the retaining nut 44, left-handed threads are used on the stud 42 and in the retaining nut 44. Further, in order to enhance greater movement of the nut 44 with reference to the stud 42, the nut and stud are cut with an increased thread pitch and a greater than normal distance between the threads so that fewer turns are required to move the nut. In a preferred embodiment, the number of threads per inch is 24, the pitch or angle of the threads is 14 degrees, and the major diameter is ¼".

The components of the invention are all non-ferrous to avoid interference with the MRI. All hardware/fasteners are brass and the bite plate 18 is plexiglass. The main bracket 30, the intermediary bracket 32, and the clamping bracket 34 are made of DELRIN®, a synthetic resinous plastic material available from E. I. Du Pont de Nemours and Company. DELRINO material was chosen because it is lightweight, offers good machining capabilities, and is relatively sturdy and non-brittle. Other MRI compatible materials would be equally acceptable.

Another aspect of the invention is a method of imaging a patient's head, free of imaging enhancements that compensate for patient movement, that include the steps of preparing a dental impression compound and affixing the idental impression compound 22 onto the bite plate 18. A dental impression 38 of the patient's bite is then taken with the dental impression compound affixed to the bite plate 18. It has been found that an impression of approximately four to six front teeth is sufficient for maintaining stability and is much more comfortable to the patient than a full mouthpiece. The dental impression is then allowed to harden and the bite plate 18 is rigidly attached to the MRI headcoil. After making approximate adjustments of the bite plate to the patient, and then making a precise adjustment of the bite plate to the patient's teeth, the patient's head is then rigidly fixed relative to the headcoil. Imaging the relatively fixed patient head can then be accomplished without the aforementioned imaging enhancements.

The dental impression compound may be prepared and applied to the bite plate in advance of the patient's arrival and conveniently stored. Once the patient arrives, it can be softened with hot water for taking the actual dental impression of the patient. The impression may be saved for future use with that patient to ensure fairly consistent head placement, or the impression compound can be broken off the bite plate once the procedure is complete and the bite plate reused after sterilization.

The present invention has been described in terms of the preferred embodiment, and it is recognized that equivalents, alternatives, and modifications, aside from those expressly stated, are possible and within the scope of the appending claims.

We claim:

1. An apparatus for immobilizing a patient's head within an MRI headcoil comprising:
   a bite plate having a first end for engagement within a patient's mouth and a second end extending outwardly and having an elongated adjustment slot therein; and
   a mounting bracket assembly having the bite plate adjustably mounted thereon to allow fore and aft adjustment of the bite plate, the mounting bracket assembly having a plurality of slots, each configured to accept a headcoil rung therein, and having a clamping plate adapted to secure at least one headcoil rung between the mounting bracket assembly and the clamping plate.

2. The apparatus of claim 1 wherein the mounting bracket assembly further comprises. An intermediary mounting bracket having the bite plate adjustably mounted to one end, and having a second end adjustably mounted to a main section of the mounting bracket assembly.

3. The apparatus of claim 1 further comprising a replaceable dental impression attached to the first end of the bite plate, the dental impression formed by a patient's bite thereby providing positive engagement between the apparatus and the patient.

4. The apparatus of claim 1 further comprises a patient adjustable set screw for locking the bite plate to the mounting bracket assembly.

5. An apparatus for immobilizing a patient's head for use within a standard MRI headcoil comprising:
   a bite plate having a first end fitted with a replaceable dental impression for engagement with a patient's teeth and a second end extending outwardly and having an elongated adjustment slot therein; and
   a mounting bracket assembly comprising a main bracket, an intermediary bracket, and a clamping plate, wherein the intermediary bracket is adjustably mounted to the main bracket for making approximate adjustments of the mounting bracket assembly to the patient, and the bite plate is adjustably mounted to the intermediary bracket for precise fore and aft adjustments of the bite plate to the patient, and wherein the main bracket of the mounting bracket assembly has a plurality of slots, each configured to accept a headcoil rung thereon, and wherein the clamping plate is attachable to the main bracket to secure at least one headcoil rung to the mounting bracket assembly; and
   a patient adjustable retainer locking the bite plate to the intermediary bracket.

6. A head restraint for use in MRI comprising:
   a main mounting bracket having two outwardly extending chamfered corners, each adapted to engage one of a first and second head coil rung, and a generally centrally arranged channel between the corners and sized to accept a third headcoil rung;
   a means for locking at least one of the headcoil rungs to the main mounting bracket; and
   a means for engaging the main mounting bracket to a patient's head to thereby immobilize the patients head with reference to the headcoil.

7. The restraint of claim 6 wherein the means for locking has a channel for receiving an inside surface of the third headcoil rung such that the headcoil is positively engaged on at least two sides to prevent relative movement of the headcoil with respect to the restraint.

8. The restraint of claim 6 wherein the main mounting bracket has an undercut about the central channel to engage the locking means with the main mounting bracket.

9. The restraint of claim 6 wherein the means for engaging comprises a slidable plate having a dental impression means thereon for custom fitting the engagements means to each patient.

10. The restraint of claim 9 further comprising an intermediary mount for slidably attaching the patient engaging means to the main mounting bracket.

11. The restraint of claim 6 wherein the means for engaging comprises a slidable plate for performing precise adjustments between the patient and the engagement means.

12. The restraint of claim 10 further comprising an adjustment means operable by the patient for performing the precise adjustments and locking the slidable plate to the main mounting bracket.

13. A method of imaging a patient head free of imaging enhancements that compensate for patient movement comprising the steps of:

preparing a dental impression compound; affixing the dental impression compound onto a bite plate;

taking a dental impression of a patient's bite with the dental impression compound affixed to the bite plate;

allowing the dental impression to harden;

rigidly attaching the bite plate to (the headcoil and to the patient head such that the patient head is relatively fixed with reference to the headcoil; and imaging the relatively fixed patient head.

14. The method of claim 13 further comprising the step of adjustably affixing the bite plate to a mounting bracket and making an approximate adjustment of the bite plate to the patient.

15. The method of claim 14 further comprising the step of making a precise adjustment of the bite plate to the patient.

* * * * *

UNITED STATES PATENT AND TRADEMARK OFFICE
CERTIFICATE OF CORRECTION

PATENT NO. : 5,836,878
DATED : November 17, 1998
INVENTOR(S) : Bryan J. Mock and William G. Irwin Jr., both of Wisconsin.

It is certified that error appears in the above-identified patent and that said Letters Patent is hereby corrected as shown below:

Column 1, line 4, insert the follwing :

GOVERNMENT RIGHTS

This invention was made with United States government support awarded by the following agencies:
NIH, Grant No: MH52354; HD03352

The United States has certain rights in this invention.

Column 3, line 38, delete "of";

Signed and Sealed this

Fourth Day of May, 1999

Q. TODD DICKINSON

Attest:

Attesting Officer

Acting Commissioner of Patents and Trademarks

UNITED STATES PATENT AND TRADEMARK OFFICE
CERTIFICATE OF CORRECTION

PATENT NO. : 5,836,878
DATED : November 17, 1998
INVENTOR(S) : Bryan J. Mock and William G. Irwin Jr., both of Wisconsin.

It is certified that error appears in the above-identified patent and that said Letters Patent is hereby corrected as shown below:

Column 6, line 2, after " stud" delete "."

Column 7, line 18, delete "DELRINO" and substitute therefor --DELRIN®--;

Claim 6, line 3, after "each" insert --corner--;

Claim 9, line 3 delete "engagements" and substitute therefor --engagement--; and Claim 13, line 9, delete "(the" and substitute therefor --the--.

Signed and Sealed this

Fourth Day of May, 1999

Q. TODD DICKINSON

*Attest:*

*Attesting Officer*

Acting Commissioner of Patents and Trademarks